US00PP29694P2

(12) United States Plant Patent
Nishikawa

(10) Patent No.: US PP29,694 P2
(45) Date of Patent: Sep. 18, 2018

(54) ***BIDENS* PLANT NAMED 'KOIBID1510'**

(50) Latin Name: *Bidens ferulifolia*
Varietal Denomination: Koibid1510

(71) Applicant: Koichiro Nishikawa, Okayama (JP)

(72) Inventor: Koichiro Nishikawa, Okayama (JP)

( * ) Notice: Subject to any disclaimer, the term of this patent is extended or adjusted under 35 U.S.C. 154(b) by 0 days.

(21) Appl. No.: 15/731,524

(22) Filed: Jun. 21, 2017

(51) Int. Cl.
*A01H 5/02* (2018.01)

(52) U.S. Cl.
USPC ..... Plt./410
CPC ..... *A01H 5/02* (2013.01)

(58) Field of Classification Search
USPC ..... Plt./410
CPC ..... A01H 5/02
See application file for complete search history.

(56) References Cited

PUBLICATIONS

PLUTO UPOVROM Plant Variety Database Citation as per CA PBR 15-8556; Apr. 30, 2015; 1 page.*
https://www.provenwinners.com/plants/bidens/carnpfire-fireburst-bidens-hybrid-0; 2018; 3 pages.*

* cited by examiner

*Primary Examiner* — Kent L Bell
(74) *Attorney, Agent, or Firm* — C. A. Whealy

(57) ABSTRACT

A new and distinct cultivar of *Bidens* plant named 'Koibid1510', characterized by its compact, upright to outwardly spreading and mounding plant habit; moderately vigorous growth habit; freely branching habit; freely flowering habit; long flowering period; and single-type inflorescences with bright yellow and dark greyed orange bi-colored ray florets and yellow green-colored disc florets.

1 Drawing Sheet

Botanical designation: *Bidens ferulifolia.*
Cultivar denomination: 'KOIBID1510'.

BACKGROUND OF THE INVENTION

The present invention relates to a new and distinct cultivar of *Bidens* plant, botanically known as *Bidens ferulifolia* and hereinafter referred to by the name 'Koibid1510'.

The new *Bidens* plant is a product of a planned breeding program conducted by the Inventor in Okayama-ken, Japan. The objective of the breeding program is to create new freely-branching *Bidens* plants with unique ray floret coloration.

The new *Bidens* plant originated from a self-pollination made by the Inventor in Okayama-ken, Japan in January, 2011 of *Bidens ferulifolia* 'K-1105', not patented. The new *Bidens* plant was discovered and selected by the Inventor as a single flowering plant from within the progeny of the stated self-pollination in a controlled greenhouse environment in Okayama-ken, Japan in May, 2011.

Asexual reproduction of the new *Bidens* plant by vegetative cuttings in a controlled environment in Okayama-ken, Japan since June, 2011 has shown that the unique features of this new *Bidens* plant are stable and reproduced true to type in successive generations.

SUMMARY OF THE INVENTION

Plants of the new *Bidens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Koibid1510'. These characteristics in combination distinguish 'Koibid1510' as a new and distinct *Bidens* plant:

1. Compact, upright to outwardly spreading and mounding plant habit.
2. Moderately vigorous growth habit.
3. Freely branching habit.
4. Freely flowering habit.
5. Long flowering period.
6. Single-type inflorescences with bright yellow and dark greyed orange bi-colored ray florets and yellow green-colored disc florets.

Plants of the new *Bidens* differ primarily from plants of the parent, 'K-1105' in growth habit as plants of the new *Bidens* are more vigorous and larger than plants of 'K-1105'. In addition, plants of the new *Bidens* and 'K-1105' differ in ray floret color as plants of 'K-1105' have deep red-colored ray florets.

Plants of the new *Bidens* can be compared to plants of *Bidens triplinervia* 'KOIBID1346', disclosed in U.S. Plant patent application Ser. No. 14/756,434 (abandoned). In side-by-side comparisons, plants of the new *Bidens* differ primarily from plants of 'KOIBID1346' in the following characteristics:

1. Plants of the new *Bidens* are more compact than and not as vigorous as plants of 'KOIBID1346'.
2. Plants of the new *Bidens* have slightly larger inflorescences than plants of 'KOIBID1346'.
3. Plants of the new *Bidens* have shorter peduncles than plants of 'KOIBID1346'.

Plants of the new *Bidens* can also be compared to plants of *Bidens ferulifolia* 'Beedance Painted Red', not patented.

In side-by-side comparisons, plants of the new *Bidens* differ primarily from plants of 'Beedance Painted Red' in the following characteristics:

1. Plants of the new *Bidens* are more vigorous than plants of 'Beedance Painted Red'.
2. Ray florets of plants of the new *Bidens* are more narrow than ray florets of plants of 'Beedance Painted Red'.

BRIEF DESCRIPTION OF THE PHOTOGRAPHS

The accompanying photographs illustrate the overall appearance of the new *Bidens* plant showing the colors as true as it is reasonably possible to obtain in colored reproductions of this type. Colors in the photographs may differ slightly from the color values cited in the detailed botanical description which accurately describe the colors of the new *Bidens* plant.

The photograph at the bottom of the sheet is a side perspective view of a typical flowering plant of 'Koibid1510' grown in a container.

The photograph at the top of the sheet is a close-up view of a typical flowering plant of 'Koibid1510'.

DETAILED BOTANICAL DESCRIPTION

The aforementioned photographs and following observations and measurements describe plants grown during the winter in 11.5-cm containers in an acrylic-covered greenhouse in Carleton, Mich. and under cultural practices typical of commercial *Bidens* production. During the production of the plants, day and night temperatures ranged from 18° C. to 27° C. Plants were eleven weeks old when the photographs and description were taken. In the following description, color references are made to The Royal Horticultural Society Colour Chart, 2007 Edition, except where general terms of ordinary dictionary significance are used.

Botanical classification: *Bidens ferulifolia* 'Koibid1510'.

Parentage: Self-pollination of *Bidens ferulifolia* 'K-1105', not patented.

Propagation:

*Type*.—By vegetative tip cuttings.

*Time to initiate roots, summer*.—About one week at temperatures about 23° C.

*Time to initiate roots, winter*.—About two weeks at temperatures about 23° C.

*Time to produce a rooted young plant, summer*.—About three to four weeks at temperatures about 23° C.

*Time to produce a rooted young plant, winter*.—About four to five weeks at temperatures about 10° C. to 15° C.

*Root description*.—Fine, fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant and growth habit*.—Compact, upright to outwardly spreading and mounding plant habit; moderately vigorous growth habit and moderate growth rate.

*Branching habit*.—Freely branching habit with about 24 primary lateral branches each with six to eight secondary lateral branches developing per plant; dense and bushy appearance.

*Plant height*.—About 21.5 cm.

*Plant diameter or spread*.—About 28 cm.

*Lateral branches*.—Length: About 12.5 cm. Diameter: About 2 mm. Internode length: About 1 cm to 1.5 cm. Strength: Strong, flexible. Aspect: Upright to outwardly. Texture and luster: Pubescent; matte. Color, developing: Close to 147C. Color, developed: Close to 148B tinged with close to 200D.

Leaf description:

*Arrangement*.—Opposite, simple with deep parallel sinuses.

*Length*.—About 3 cm.

*Width*.—About 2.5 cm.

*Shape*.—Palmate; leaf lobes are lanceolate to elliptic.

*Apex*.—Acute.

*Base*.—Attenuate.

*Margin*.—Deeply incised; serrate to serrulate.

*Texture and luster, upper and lower surfaces*.—Minute pubescence; matte.

*Venation pattern*.—Pinnate.

*Color*.—Developing leaves, upper surface: Close to 146A. Developing leaves, lower surface: Close to 146B. Fully expanded leaves, upper surface: Close to 147A; venation, close to 147B. Fully expanded leaves, lower surface: Close to 147C; venation, close to 147C.

*Petioles*.—Length: About 1.5 cm. Diameter: About 1 mm. Strength: Moderately strong, flexible. Texture and luster, upper and lower surfaces: Minute pubescence; matte. Color, upper surface: Close to 197B. Color, lower surface: Close to 195A.

Inflorescence description:

*Appearance*.—Single type (daisy) solitary inflorescences developing on terminal and axillary peduncles; inflorescence form with ray and disc florets; inflorescences positioned on moderately strong peduncles; inflorescences face mostly upright.

*Flowering habit*.—Freely flowering habit with more than 450 inflorescences and inflorescence buds developing during the flowering season.

*Fragrance*.—None detected.

*Flowering response*.—Early flowering habit, plants begin flowering about seven weeks after planting.

*Natural flowering season*.—Long flowering period, plants flower continuously from spring until frost in temperate regions and year-round in milder (above freezing) climates.

*Inflorescence longevity*.—Inflorescences last about seven days on the plant; inflorescences persistent.

*Inflorescence buds*.—Height: About 8 mm. Diameter: About 7 mm. Shape: Rounded to oval. Texture and luster: Scattered pubescence; slightly glossy. Color: Close to 151A.

*Inflorescence size*.—Overall diameter: About 3.5 cm to 4.5 cm. Overall height: About 8 mm to 9 mm. Disc diameter: About 7 mm.

*Receptacles*.—Receptacle diameter: About 1 cm. Receptacle height: About 4 mm. Receptacle shape: Small, cup-shaped. Receptacle color: Close to 148B.

*Ray florets*.—Number of ray florets per inflorescence: About five to seven arranged in a single whorl. Length: About 2 cm. Width: About 1 cm. Shape: Elliptical. Apex: Shallowly emarginate. Base: Attenuate. Margin: Entire. Aspect: Mostly horizontal, apices reflexing with development. Texture and luster, upper and lower surfaces: Longitudinally ribbed, glabrous; matte. Color: When opening, upper surface: Distally, close to 187A; proximally, close to 14A. When opening, lower surface: Distally, close to N199A; proximally, close to 12A. Fully opened, upper surface: Distally, darker than 175A; proximally, close to 14A; venation, similar to lamina; colors do not fade with development. Fully opened, lower surface: Distally, close to 166B to 166C; proximally, close to 12A; venation, close to 145B; colors do not fade with development.

*Disc florets*.—Number of disc florets per inflorescence: About 70 in about six whorls at the center of the receptacle. Length: About 8 mm. Diameter: About 1 mm. Shape: Tubular, slender; apex, five-pointed. Texture and luster: Smooth, glabrous; slightly glossy. Color: When opening, inner and outer surfaces: Close to 153D. Fully opened, inner and outer surfaces: Close to 151D.

*Phyllaries*.—Quantity per inflorescence: About 16 to 18 arranged in about two whorls. Length: About 5 mm to 7 mm. Width: About 1 mm. Shape: Lanceolate. Apex: Acute. Base: Truncate. Margin: Entire. Aspect: Slightly reflexed. Texture and luster, upper and lower surfaces: Scattered pubescence; matte to slightly glossy. Color, upper surface: Close to 146D. Color, lower surface: Close to 147A.

*Peduncles*.—Length, terminal peduncle: About 3.4 cm. Length, third peduncle: About 6.5 cm. Diameter: About 1 mm. Strength: Moderately strong; flexible. Aspect: Terminal peduncles, mostly erect; axillary peduncles, about 45° from vertical. Texture and luster: Minute pubescence; matte. Color: Close to 146B.

*Reproductive organs*.—Present on disc florets only; ray florets without visible reproductive organs. Androecium: Quantity per disc floret: Five. Filament length: About 2 mm. Filament color: Close to 145D. Anther shape: Lanceolate. Anther length: About 2 mm. Anther color: Close to 200A. Pollen amount: Scarce. Pollen color: Close to 16A. Gynoecium: Quantity per disc floret: One. Pistil length: About 4 mm. Style length: About 2 mm. Style color: Close to 145D. Stigma shape: Bi-parted. Stigma color: Close to 14A. Ovary color: Close to 145D.

*Seeds and fruits*.—Seed and fruit development have not been observed on plants of the new *Bidens* to date.

Disease & pest resistance: Plants of the new *Bidens* have not been shown to be resistant to pathogens and pests common to *Bidens* plants.

Garden performance: Plants of the new *Bidens* have been observed to have good garden performance and to tolerate temperatures from about 1° C. to about 40° C. and are suitable for USDA Hardiness Zones 9 and 11.

It is claimed:

1. A new and distinct *Bidens* plant named 'Koibid1510' as illustrated and described.

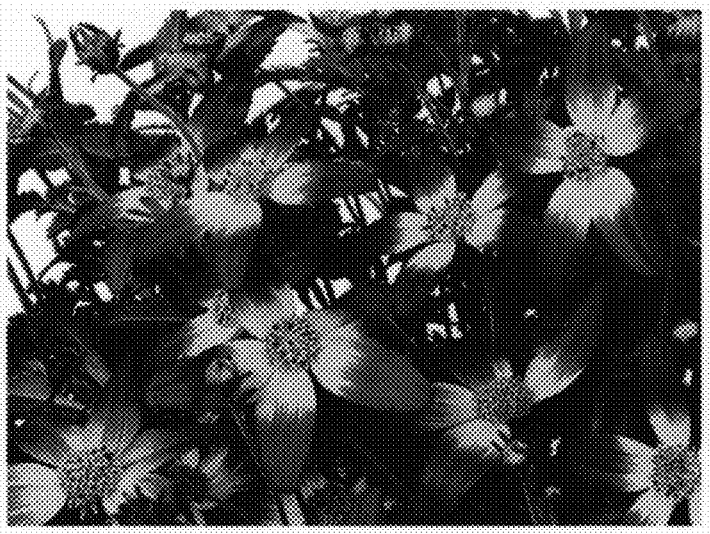
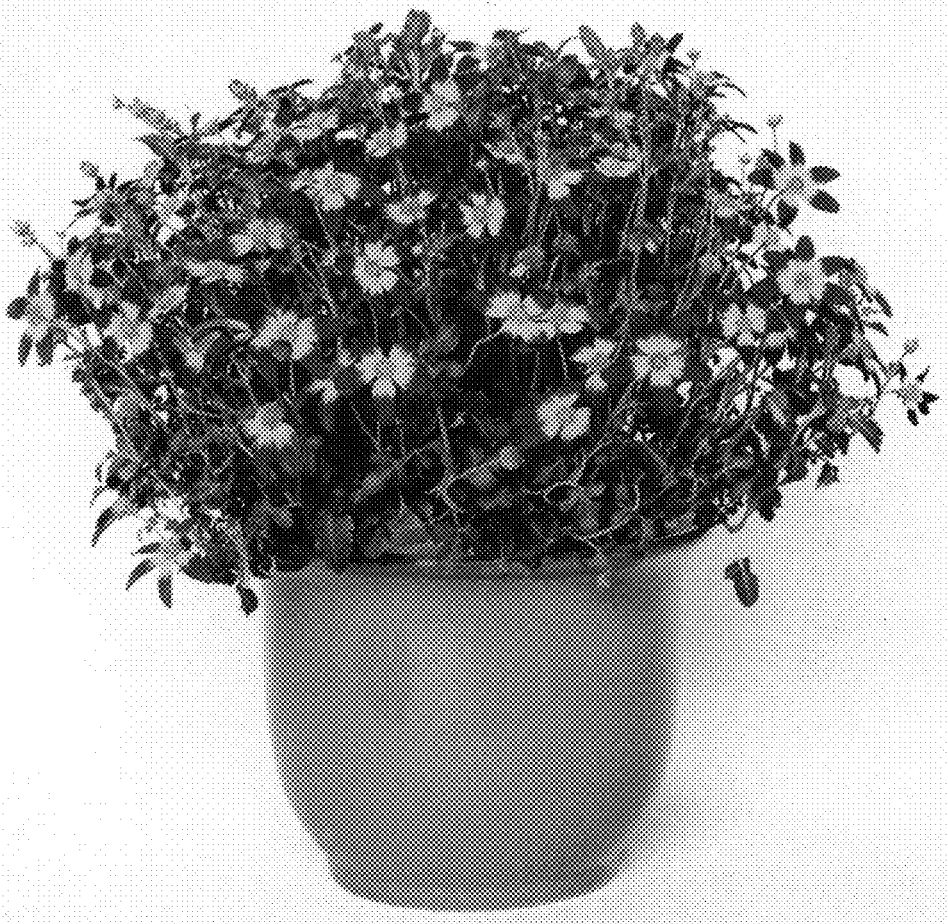

* * * * *